(12) United States Patent
Ding et al.

(10) Patent No.: US 8,404,091 B2
(45) Date of Patent: Mar. 26, 2013

(54) DIALYSIS TREATMENT DEVICES FOR REMOVING UREA

(75) Inventors: Yuanpang Samuel Ding, Libertyville, IL (US); Ying-Cheng Lo, Green Oak, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 840 days.

(21) Appl. No.: 12/548,876

(22) Filed: Aug. 27, 2009

(65) Prior Publication Data

US 2011/0048949 A1  Mar. 3, 2011

(51) Int. Cl.
*B01D 61/44* (2006.01)
(52) U.S. Cl. ......... 204/527; 204/540; 204/633; 204/634
(58) Field of Classification Search .................. 204/527, 204/540, 633, 634
See application file for complete search history.

(56) References Cited

U.S. PATENT DOCUMENTS

| | | | |
|---|---|---|---|
| 3,617,545 A | 11/1971 | Dubois et al. | |
| 3,799,873 A | 3/1974 | Brown | |
| 4,687,561 A * | 8/1987 | Kunz ............................ 204/524 |
| 5,244,568 A | 9/1993 | Lindsay et al. | |
| 5,247,434 A | 9/1993 | Peterson et al. | |
| 5,350,357 A | 9/1994 | Kamen et al. | |
| 5,662,806 A | 9/1997 | Keshaniah et al. | |
| 5,873,853 A | 2/1999 | Keilman et al. | |
| 5,984,891 A | 11/1999 | Keilman et al. | |
| 6,196,992 B1 | 3/2001 | Keilman et al. | |
| 6,592,542 B2 | 7/2003 | Childers et al. | |
| 7,318,892 B2 | 1/2008 | Connell et al. | |
| 2003/0097086 A1 | 5/2003 | Gura | |
| 2007/0213665 A1 | 9/2007 | Curtin et al. | |
| 2008/0051696 A1 | 2/2008 | Curtin et al. | |

FOREIGN PATENT DOCUMENTS

WO  2008/020801  2/2008

OTHER PUBLICATIONS

International Search Report for PCT/US2010/045990 mailed Nov. 15, 2010, 5 pages.
Written Opinion of the International Searching Authority for PCT/US2010/045990 mailed Nov. 15, 2010, 8 pages.

* cited by examiner

*Primary Examiner* — Arun S Phasge
(74) *Attorney, Agent, or Firm* — K&L Gates LLP (57) ABSTRACT

Dialysis treatment devices and methods for removing urea from dialysis waste streams are provided. In a general embodiment, the present disclosure provides a dialysis treatment device including a first cell having a first electrodialysis unit, a second cell having at least one of a urease compartment and a sorbent compartment and in fluid communication with the first cell, and a third cell having a second electrodialysis unit and in fluid communication with the second cell.

20 Claims, 4 Drawing Sheets

DIALYSIS TREATMENT DEVICES FOR REMOVING UREA

BACKGROUND

The present disclosure relates to the general field of dialysis treatment devices and methods, and in particular, for removing urea from dialysis waste streams.

Hemodialysis and peritoneal dialysis are two types of dialysis therapies used commonly to treat loss of kidney function. A hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane, and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

APD is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, dialysis systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia (e.g., ammonium cation). The ammonia is then removed from the dialysate by adsorption prior to reintroduction of the dialysate into the peritoneal cavity. Additional sensors are employed to monitor the removal of ammonia. CFPD systems are typically more complicated than batch systems.

In both hemodialysis and peritoneal dialysis, "sorbent" technology can be used to remove uremic toxins from waste dialysate, re-inject therapeutic agents (such as ions and/or glucose) into the treated fluid, and reuse that fluid to continue the dialysis of the patient. One commonly used sorbent is made from zirconium phosphate, which is used to remove ammonia generated from the hydrolysis of urea. Typically, a large quantity of sorbent is necessary to remove the ammonia generated during dialysis treatments.

The main advantage of the sorbent based approach is that lower volumes of dialysis fluid or dialysate are required to achieve high volume dialysis treatments. The main disadvantage of the sorbent system is the high cost of the sorbent disposable, the amount of space required to house the sorbent, and concerns regarding the purity of the recycled solution, as many ions remain in the fluid after treatment and verification of purity is technically challenging to perform.

SUMMARY

The present disclosure provides dialysis treatment devices and methods that treat dialysis waste streams during hemodialysis and peritoneal dialysis. In a general embodiment, the present disclosure provides a dialysis treatment device having a first cell including a first electrodialysis unit, a second cell having at least one of a urease compartment and a sorbent compartment and in fluid communication with the first cell, and a third cell including a second electrodialysis unit and in fluid communication with the second cell.

The dialysis treatment device can be contained within a cartridge for a wearable artificial kidney. The cartridge can be configured to be removable and/or disposable. In an embodiment, the first cell and third cell are fixedly contained within the cartridge for a wearable artificial kidney. The second cell can then be removably attached from and in fluid communication with the first cell and the third cell.

In an embodiment, the third cell further includes an ammonia sorbent. Each of the first, second and third cells can include at least two corresponding fluid pathways. The first cell can include one or more cation exchange membranes and anion exchange membranes. The third cell can also include one or more cation exchange membranes and anion exchange membranes. In an embodiment, the dialysis treatment device further includes an activated carbon unit in fluid communication with the first cell.

In another embodiment, the present disclosure provides a dialysis treatment device including a first cell having an electrodialysis unit with a cathode and two opposing anodes, and a second cell having a urease compartment and a sorbent compartment and in fluid communication with the first cell. The first cell can further include an ammonia sorbent. The second cell can further include at least one of a phosphate binder compartment and an anion exchange sorbent component.

In an embodiment, the first cell can be fixedly contained within a cartridge for a wearable artificial kidney. The second cell can be removably attached to a cartridge for a wearable artificial kidney. The first cell can include one or more cation exchange membranes and/or anion exchange membranes. The sorbent cartridge of the second cell can include activated carbon.

In an alternative embodiment, the present disclosure provides a method for removing urea from a dialysis fluid. The method includes circulating the dialysis fluid in a fluid circuit that includes a dialysis apparatus having a cartridge including an electrodialysis unit and a urea removal unit. The method further includes removing urea from the dialysis fluid via the cartridge, and recirculating the dialysis fluid back to a patient. The urea removal unit can be a separately disposable unit that is removable from the dialysis apparatus. For example, the urea removal unit can be detachable from the dialysis apparatus without having to remove the entire electrodialysis unit.

It is accordingly an advantage of the present disclosure to provide an improved dialysis treatment device.

It is another advantage of the present disclosure to provide an improved urea removal cartridge.

It is yet another advantage of the present disclosure to provide a urea removal cartridge for a wearable artificial kidney.

Still further, it is an advantage of the present disclosure to provide a urea removal cartridge for a wearable artificial kidney having a reduced ammonia sorbent requirement.

Another advantage of the present disclosure to provide an improved method for removing urea from a dialysis waste stream.

Additional features and advantages are described herein, and will be apparent from the following Detailed Description and the figures.

DETAILED DESCRIPTION

The present disclosure relates to dialysis treatment devices and methods for removing urea from dialysis waste streams during hemodialysis or peritoneal dialysis. The dialysis treatment devices are constructed and arranged to reduce the amount of sorbents needed for removing urea from the dialysis waste stream as compared to current technologies. This can significantly reduce the cost, size and complexity of dialysis treatments systems that remove urea.

The dialysis treatment devices and methods can be used and implemented in various hemodialysis and peritoneal dialysis technologies such as, for example, those described in U.S. Pat. Nos. 5,244,568, 5,247,434, 5,350,357, 5,662,806, 6,592,542 and 7,318,892, which are incorporated herein by reference. The hemodialysis and peritoneal dialysis technologies can be designed and configured for medical centers and be implemented with on-site or at-home dialysis treatments. The dialysis treatment devices and methods can further be used in portable dialysis treatment devices such as, for example, wearable artificial kidneys in which a patient may move freely during dialysis. Non-limiting examples of portable dialysis treatment devices are described in U.S. Pat. Nos. 5,873,853, 5,984,891 and 6,196,992 and U.S. Patent Publication Nos. 2007/0213665 and 2008/0051696, which are incorporated herein by reference.

Figure 1:
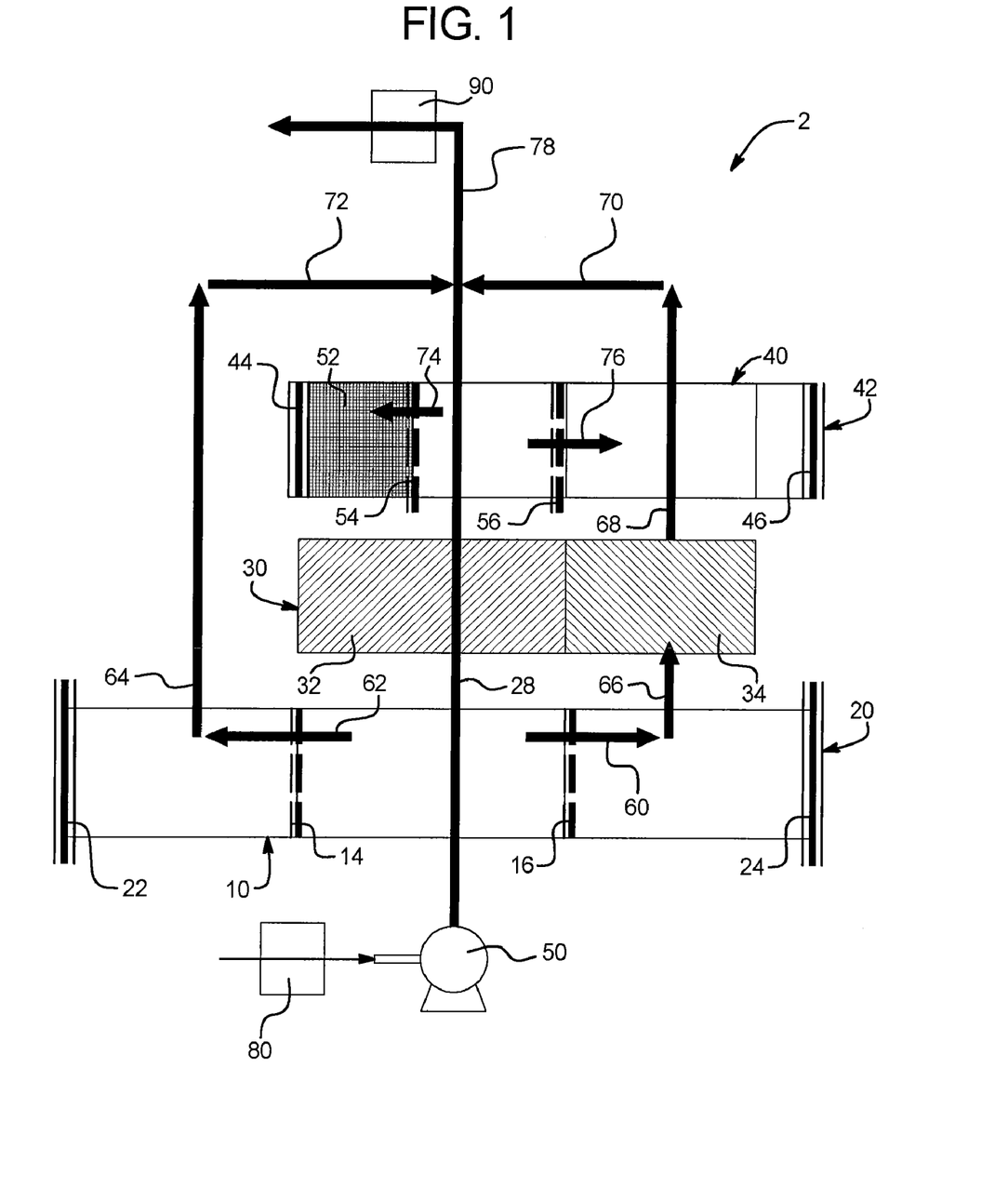
FIG. 1 is a schematic illustration of a dialysis treatment device using multiple electrodialysis units in an embodiment of the present disclosure.

Referring now to the drawings and in particular to FIG. 1, one embodiment of a dialysis treatment device 2 of the present disclosure is illustrated. The dialysis treatment device 2 includes a first cell 10 having a first electrodialysis ("ED") unit 20, which is in fluid communication with a second cell 30 having urease. Second cell 30 is in fluid communication with a third cell 40 having a second ED unit 42. Dialysis treatment device 2 can be sized and configured to be contained within a treatment cartridge for a portable dialysis treatment devices such as, for example, wearable kidneys. The treatment device 2 or the individual components of the treatment device 2 (e.g., second cell) in such cases can be disposable or reusable.

First cell 10 has a cathode 22 at one end and an anode 24 at the opposing end to form first ED unit 20. First cell 10 can further include a cation exchange membrane 14 and/or an anion exchange membrane 16. First ED unit 20 is used to transport salt ions from the dialysis waste stream through the ion-exchange membranes to another dialysis fluid stream under the influence of an applied electric potential difference between cathode 22 and anode 24.

Second cell 30 includes a urease compartment 32 and/or a sorbent compartment 34. It should be appreciated that urease compartment 32 and sorbent compartment 34 can be attached to each other as part of an integral unit or be used apart from each other. Urease compartment 32 contains urease, an enzyme that catalyzes the hydrolysis of urea into carbon dioxide (e.g., bicarbonate) and ammonia (e.g., ammonium cation). Urea from the dialysis waste stream is exposed to the urease at this location. The urease can be contained in urease compartment 32 in any suitable manner. For example, the urease can be immobilized in a layer of beads or resins or be cross-linked urease enzyme crystals impregnated as part of a sorbent or membrane. Sorbent compartment 34 can contain sorbents (e.g., hydrous zirconium oxide) suitably designed to remove ions, for example, such as phosphate ($HPO_4^{2-}$) and desirably also sulfate ($SO_4^{2-}$). Second cell 30 is in fluid communication with first cell 10 via flow paths 28 and 66, which can be tubed pathways or pathways formed as part of the treatment device 2.

Third cell 40 has a cathode 44 at one end and an anode 46 at the opposing end to form a second ED unit 42. Third cell 40 can further include an ammonia sorbent 52 (e.g zirconium phosphate). Third cell 40 can also include one or more cation exchange membranes 54 and/or anion exchange membrane 56 as illustrated in FIG. 1. Third cell 40 is in fluid communication with second cell 30 via flow paths 28 and 68, which can be configured as described for pathways 28 and 66. Fluid pathways 28 and 68 can be parallel to each other and be used to connect first, second and third cells 10, 30 and 40 in a fixed or separable manner. Fluid flow paths 28 and 68 can combine to form a single outlet fluid flow path 78 for subsequent patient treatment/recirculation. In the illustrated embodiment, pump 50 pumps spent dialysis fluid from the patient, through treatment device 2 via line 28, and back to the patient.

In an alternative embodiment, dialysis treatment device 2 includes an adsorption or carbon compartment 80 in fluid communication with (e.g., upstream) first cell 10. In this manner, organic toxins of the dialysis waste stream can be removed from the waste stream prior to entering first cell 10 through adsorption onto an adsorption layer surface of the carbon (e.g., activated carbon or other appropriate organic neutralizing surface).

In another embodiment, dialysis treatment device 2 includes a supplementary ammonia sorbent unit 90 along fluid flow path 78 subsequent to third cell 40 as a precautionary measure to completely remove any ammonia from the fluid that passes through dialysis treatment device 2. In an embodiment, the supplementary ammonia sorbent unit 90 is placed before the joint with fluid paths 70 and 72. The ammonia sorbent unit can include any suitable ammonia sorbent such as, for example, zirconium phosphate to trap any residual ammonia in the treated fluid stream.

In an embodiment, first ED unit 20 and second ED unit 42 can be integrated in a portable or stand-alone dialysis treatment unit. In this regard, second cell 30 can be individually contained within a removable cassette or cartridge while still using the apparatus and flow configuration of dialysis treatment device 2. For example, second cell 30 and/or components thereof such as urease compartment 30 or sorbent compartment 34 can be readily and conveniently replaced in the portable or stand-alone dialysis treatment units without having to remove either first ED unit 20 or second ED unit 42.

As seen in FIG. 1, during operation, spent dialysis fluid or a dialysis waste stream from a patient enters first cell 10 via flow path 28, in which it is exposed to first ED unit 20. At this time, ED unit 20 removes ionic species in the waste stream into side flow paths 64 and 66.

As urea is a neutral molecule, flow path 28 carrying urea travels through first cell 10 and into urease compartment 32 of second cell 30, in which the urea is converted to ammonia. From urease compartment 32, flow path 28 travels into third cell 40 where the fluid stream is exposed to second ED unit 42. Second ED unit 42 causes the ammonia (e.g., ammonium ion) in the fluid stream to enter ammonia sorbent 52 where it is removed from the fluid stream. The trapped ammonia can be flushed to drain by a separate fluid stream. Flow path 28 then exits dialysis treatment device 2 via flow path 78.

As further seen in FIG. 1, part of the spent dialysis or a dialysis waste stream in first cell 10 that is exposed to first ED unit 20 is split into separate flow paths 60 and 62. For example, in flow path 60, ion exchange takes place with anion exchange membrane 16 of first cell 10 as negatively charged species are drawn to anode 24. From fluid flow path 60, the fluid stream enters second cell 30 via flow path 66 where anions such as phosphates and sulfates are removed in sorbent compartment 34. This can generate species such as chloride, acetate and carbonate (from ion exchange) depending on the type of sorbent used in sorbent compartment 34. From sorbent compartment 34, the fluid stream travels via flow path 68 into third cell 40. In third cell 40, bicarbonate ions can mix with the fluid stream due to second ED unit 42. The fluid stream from third cell 40 combines with fluid flow path 28 via flow path 70.

The dialysis waste stream in first cell 10 that is exposed to ED unit 20 can be further split into a second separate flow path 62. Inflow path 62, ion exchange can take place with cation exchange membrane 14 of first cell 10 as positively charged species are drawn to cathode 22. The fluid stream can then pass by second cell 30 and third cell 40 to combine with fluid flow path 28 via flow path 72. In an alternative embodiment, second cell 30 and/or third cell 40 can contain any additional treatments units (e.g., along flow path 64) to treat the fluid in flow path 64 to provide a complete treatment and removal of any undesired wastes from the spent dialysis fluid.

The final treated dialysate stream exiting the dialysis treatment device 2 via flow path 78 can be taken for further re-circulation as fresh dialysate or treatment (e.g., ion exchange). In addition, ions and/or fluids can be replaced in the stream, for example, through the addition of concentrated dialysis components such as osmotic agents (e.g., dextrose, icodextrin, glucose polymers, glucose polymer derivatives, amino acids), buffers (e.g., lactate, bicarbonate) and electrolytes (e.g., sodium, potassium, calcium, magnesium) from a suitable fluid source.

Figure 2:
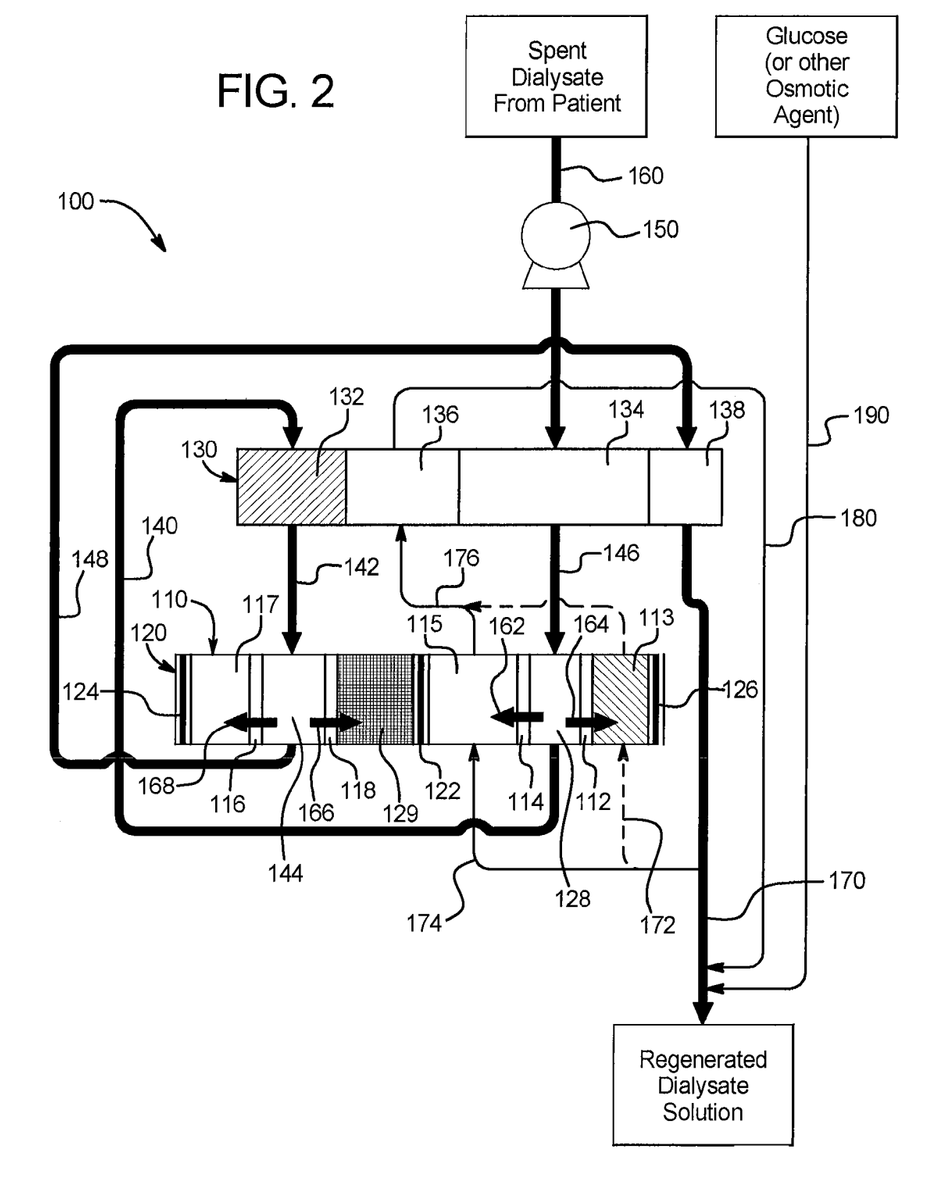
FIG. 2 is a schematic illustration of a dialysis treatment device using multiple electrodialysis units in a second embodiment of the present disclosure.

In another embodiment illustrated in FIG. 2, a dialysis treatment device 100 includes a first cell 110 having an ED unit 120, which is in fluid communication with a second cell 130 having urease. Dialysis treatment device 100 can be sized and configured to be contained within a treatment cartridge for any of the above-described types of dialysis treatment devices. Second cell 130 can be removable and disposable. A suitable pump 150 can pump spent dialysis fluid from the patient, through treatment device 100, and back to the patient.

First cell 110 includes a cathode 122 that is positioned within first cell 110. A first anode 124 is positioned at one end and a second anode 126 is positioned at an opposing end of first cell 100 to form ED unit 120 in first cell 110. The anode and cathode fluids can be, for example, (1) water or (2) dilute HCl(aq), NaOH(aq), $H_2SO_4$(aq) and/or NaCl(aq). First cell 110 can further include one or more cation exchange membranes 114 and 118 and/or one or more anion exchange membranes 112 and 116. Here, ED unit 120 is used to transport salt ions from the dialysis waste stream through the ion-exchange membranes to another dialysis fluid stream or compartment under the influence of an applied electric potential difference between cathode 122 and anodes 124 and 126. First cell 110 can further include an ammonia sorbent compartment 129, which removes ammonia from the waste stream.

Second cell 130 can include a urease compartment 132 and a sorbent compartment 134. The urease is contained in urease compartment 132 in a suitable manner, such as, in an immobilized layer of beads or resins or cross-linked urease enzyme crystals impregnated as part of a sorbent or membrane. Sorbent compartment 134 can contain any suitable sorbent such as activated carbon. Second cell 130 can optionally include one or more additional sorbent compartments 136 and 138. For example, sorbent compartment 136 can include hydrous zirconium oxide to suitably remove ions such as phosphate ($HPO_4^{2-}$) and/or sulfate ($SO_4^{2-}$). Sorbent compartment 138 can include an ammonia sorbent such as, for example, zirconium phosphate to trap any residual ammonia in the treated fluid stream.

FIG. 2 further illustrates the fluid flow paths that lead into and out of first and second cells 110 and 130. Second cell 130 is in fluid communication with first cell 110 via flow paths 140, 142 and 146. If second cell 130 includes sorbent compartment 138, a flow path 148 can take fluid from first cell 110 to sorbent compartment 138.

In an embodiment, first cell 130 and ED unit 120 can be integrated (e.g., not removable) in a portable or stand-alone dialysis treatment unit. In this manner, second cell 130 can be an individually removable cassette or cartridge that uses the flow configuration of dialysis treatment device 100 as shown in FIG. 2. For example, second cell 130 can be readily removed and replaced in the portable or stand-alone dialysis treatment units without having to remove first cell 130 and ED unit 120.

During operation, spent dialysis fluid or a dialysis waste stream from a patient enters sorbent compartment 134 of second cell 130 via flow path 160 wherein organic toxins of the dialysis waste stream can be removed through adsorption onto the adsorption layer surface of the sorbent located in sorbent compartment 134. The fluid is transferred from sorbent compartment 134 to a compartment 128 of first cell 110 via flow path 146, in which it is exposed to ED unit 120.

As seen in FIG. 2, exposing the spent dialysis or a dialysis waste stream in compartment 128 of first cell 110 to ED unit 120 causes migration of positively charged ions in the waste stream to migrate past cation exchange membrane 114 via flow path 162 into compartment 115. Similarly, negatively charged ions in the waste stream migrate past anion exchange membrane 112 via flow path 164 into compartment 113.

From compartment 128, the fluid stream can enter second cell 130 via flow path 140 in which the fluid stream is exposed to urease compartment 132. From urease compartment 132, the fluid stream can enter compartment 144 of first cell 110. As seen in FIG. 2, exposing the spent dialysis or a dialysis waste stream in compartment 144 of first cell 110 to ED unit 120 causes migration of positively charged ions in the waste stream to migrate past cation exchange membrane 118 via flow path 166 into ammonia sorbent compartment 129 wherein ammonia can be removed. Similarly, negatively charged ions in the waste stream migrate past anion exchange membrane 116 via flow path 168 into compartment 117.

From compartment 144, the fluid stream can enter optional ammonium sorbent compartment, e.g., zirconium phosphate compartment 138 via flow path 148, which results in the regenerated dialysate solution. At this time, glucose or other suitable osmotic agents can be added to the treated fluid stream 170 via flow path 190.

In an alternative embodiment, part of the treated fluid stream (flow path 170) can be rerouted to pass through first cell 110 again via flow paths 172 and/or 174. From first cell 110, the fluid stream can pass through sorbent compartment 136 of second cell 130 via flow path 176 for additional treatment. The treated fluid stream can then re-enter flow path 170 via flow path 180 as part of the regenerated dialysate solution.

Figure 3:
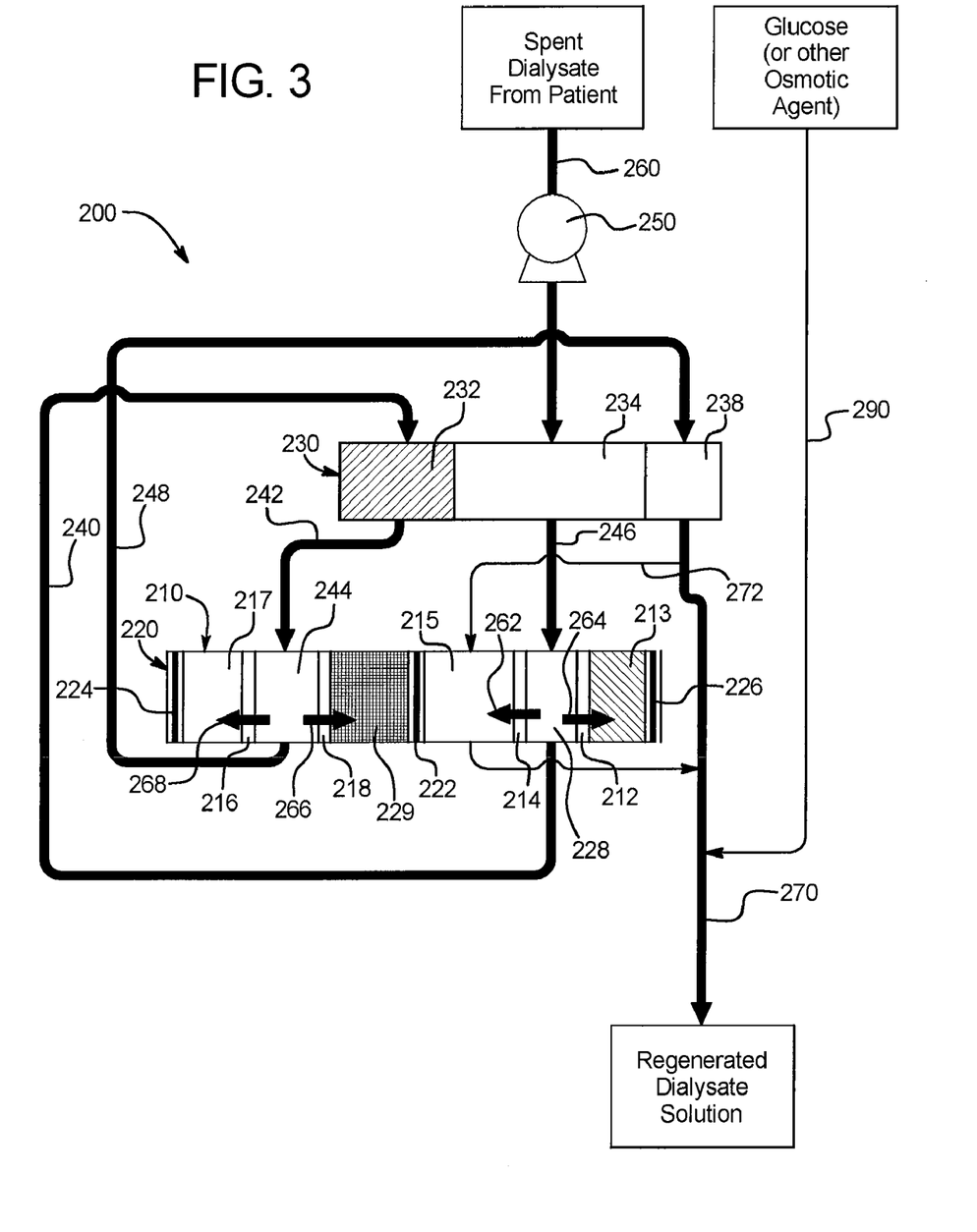
FIG. 3 is a schematic illustration of a dialysis treatment device using multiple electrodialysis units in a third embodiment of the present disclosure.

In an alternative embodiment illustrated in FIG. 3, a dialysis treatment device 200 includes a first cell 210 having an ED unit 220, which is in fluid communication with a second cell 230 having urease. Dialysis treatment device 200 can be sized and configured to be contained within a treatment cartridge for any of the above-described types of dialysis treatment devices. Second cell 230 can be removable and disposable. A suitable pump 250 (e.g., volumetric membrane or peristaltic) can pump spent dialysis fluid from the patient, through treatment device 200, and back to the patient.

First cell 210 includes a cathode 222 that is positioned within first cell 210. A first anode 224 is positioned at one end and a second anode 226 is positioned at an opposing end of first cell 200 to form ED unit 220 in first cell 210. The anode and cathode fluids can be (1) water or (2) dilute HCl(aq), NaOH(aq), $H_2SO_4$(aq) and/or NaCl(aq).

First cell 210 can further include one or more cation exchange membranes 214 and 218 and/or one or more anion exchange membranes 212 and 216. In this regard, ED unit 220 is used to transport salt ions from the dialysis waste stream through the ion-exchange membranes to another dialysis fluid stream or compartment under the influence of an applied electric potential difference between cathode 222 and anodes 224 and 226. First cell 210 can further include an ammonia sorbent 229, which removes ammonia from the waste stream.

Second cell 230 can include a urease compartment 232 and a sorbent compartment 234. The urease is contained in urease compartment 232 in a suitable manner, such as, in an immobilized layer of beads or resins or cross-linked urease enzyme crystals impregnated as part of a sorbent or membrane. Sorbent compartment 234 can contain sorbents such as activated carbon. Second cell 230 can optionally include one or more additional sorbent compartments 238. Sorbent compartment 238 can include an ammonia sorbent such as, for example, zirconium phosphate to trap any residual ammonia in the treated fluid stream.

FIG. 3 further illustrates the fluid flow paths that lead into and out of first and second cells 210 and 230. Second cell 230 is in fluid communication with first cell 210 via flow paths 240, 242 and 246. If second cell 230 includes sorbent compartment 238, a flow path 248 can take fluid from first cell 210 to sorbent compartment 238.

In an embodiment, ED unit 220 can be integrated (e.g., not removable) in a portable or stand-alone dialysis treatment unit. Second cell 230 can be a removable cartridge that uses the flow configuration of dialysis treatment device 200 as shown in FIG. 3. Here, second cell 230 can be replaced in the portable or stand-alone dialysis treatment units without having to remove ED unit 220.

During operation, spent dialysis fluid or a dialysis waste stream from a patient enters sorbent compartment 234 of second cell 230 via flow path 260 wherein organic toxins of the dialysis waste stream can be removed through adsorption onto the adsorption layer surface of the sorbent. The fluid is transferred from sorbent compartment 234 to a compartment 228 of first cell 210 via flow path 246, in which it is exposed to ED unit 220. As seen in FIG. 3, exposing the spent dialysis or a dialysis waste stream in compartment 228 of first cell 210 to ED unit 220 causes migration of positively charged ions in the waste stream to migrate past cation exchange membrane 214 via flow path 262 into compartment 215 and negatively charged ions in the waste stream to migrate past anion exchange membrane 212 via flow path 264 into compartment 213.

From compartment 228, the fluid stream can enter second cell 230 via flow path 240 where the fluid stream is exposed to urease compartment 232 for urease conversion to ammonia. From urease compartment 232, the fluid stream can enter compartment 244 of first cell 210. As seen in FIG. 3, exposing the spent dialysis or a dialysis waste stream in compartment 244 of first cell 210 to ED unit 220 causes further migration of positively charged ions in the waste stream to migrate past cation exchange membrane 218 via flow path 266 into ammonia sorbent compartment 229 for ammonia removal and negatively charged ions in the waste stream to migrate past anion exchange membrane 216 via flow path 268 into compartment 217.

From compartment 244, the fluid stream can enter optional ammonium sorbent such as, e.g., zirconium phosphate compartment 238 via flow path 248 thereby resulting in the regenerated dialysate solution. At this time, glucose or other suitable osmotic agents can be added to the treated fluid stream 270 via flow path 290.

In an alternative embodiment, part of the treated fluid stream in flow path 270 can be rerouted to pass through first cell 210 via flow path 272. For example, the treated fluid stream 270 can be diverted to compartment 215 of first cell 210 via flow path 272 to be replenished with electrolytes collected in compartment 215 (e.g., $Ca^{2+}$, $Mg^{2+}$, $Na^{2+}$, etc.). From first cell 210, the fluid stream can re-enter flow path 270 as part of the regenerated dialysate solution.

Due to the design of dialysis treatment devices 2, 100 and 200, sorbents such as zirconium phosphate, zirconium bicarbonate and/or ion exchange layers typically used for ammonia removal may be unnecessary. Alternatively, dialysis treatment devices 2, 100 and 200 allow for a reduced amount of sorbent necessary as compared to typical dialysis treatment systems using sorbents for ammonia removal.

Figure 4A:
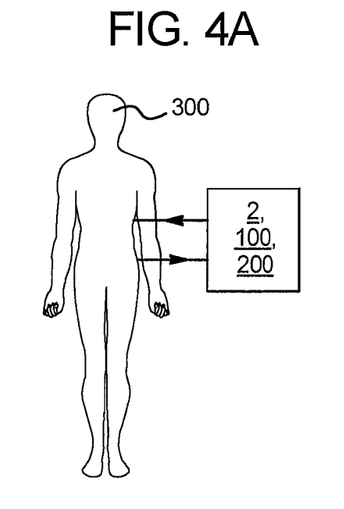
FIGS. 4A to 4D are schematic illustrations of the dialysis treatment devices used in various dialysis treatment technologies.

Any of the dialysis treatment devices 3, 100 and 200 discussed herein can be used for peritoneal dialysis ("PD"), hemodialysis ("HD"), hemofiltration ("HF") or hemodiafiltration ("HDF") as shown in FIGS. 4A to 4D, respectively. FIG. 4A illustrates a schematic of a PD treatment being performed on a patient 300. Spent dialysis fluid from patient 300 enters one of dialysis treatment devices 2, 100 and 200 for treatment/urea removal. Regenerated dialysis is returned to the patient for reuse. This can be done on a continuous basis ("CFPD"), on a batch basis in which dialysis fluid dwells within patient 300 for a period of time, or on a semi-continuous or tidal basis.

Figure 4B:
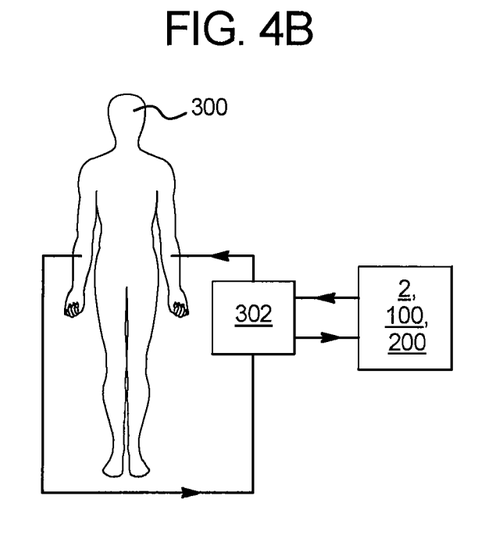

FIG. 4B illustrates a schematic of an HD treatment being performed on patient 300. Blood from patient 300 is pumped through a dialyzer 302, cleaned and returned to patient 300. Spent dialysis fluid from dialyzer 302 is sent to one of the dialysis treatment device 2, 100 and 200 for treatment/urea removal. The treated fluid is then returned to dialyzer 302 on a continuous basis to continuously clean the patients' blood.

Figure 4C:
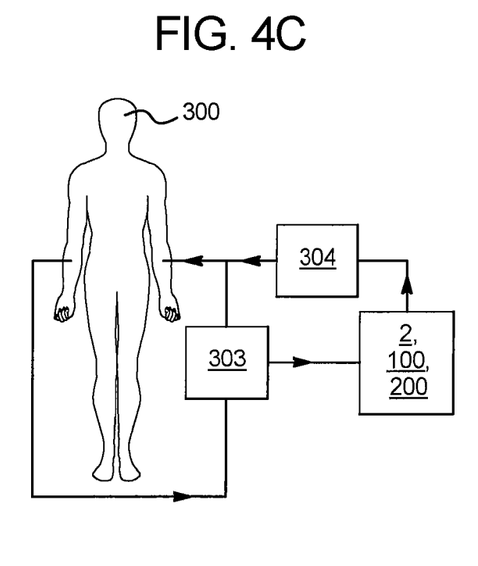

FIG. 4C illustrates a schematic of an HF treatment technology. HF is a technology similar to HD. With hemofiltration, dialysate is not used. Instead, a positive hydrostatic pressure drives water and solutes across the filter membrane of hemofilter 303 from its blood compartment to its filtrate compartment, from which it is drained. The spent dialysis fluid is sent to one of the dialysis treatment devices 2, 100 and 200 for treatment/urea removal. The treated fluid is then further purified by being sent through one or more pyrogen filters 304 such as an ultrafilter, pyrogen filter or nanofilter that removes toxins and endotoxins. The resulting replacement fluid is pumped directly into the blood causing a convective cleansing of the patient. As with PD and HD, a net volume of fluid is taken off of the patient as ultrafiltrate to remove excess water that the patient has accumulated between treatments.

Figure 4D:
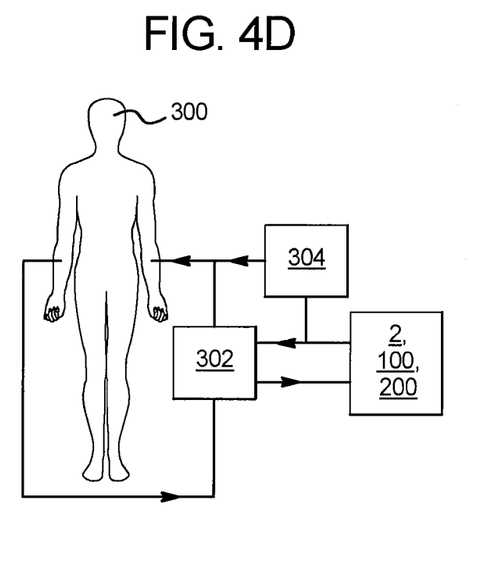

FIG. 4D illustrates a schematic of an HDF treatment technology. HDF is a combination of HD and HF. Blood is pumped through the blood compartment of dialyzer 302 in a manner similar to HD and HF. Spent dialysate is pulled from dialyzer 302 and cleaned at one of dialysis treatment devices 2, 100 and 200. The cleaned dialysate is split, some going directly back to dialyzer 302 and some pumped through one or more of a pyrogen filter, nanofilter, or ultrafilter to form a suitable replacement fluid that is pumped directly into the patient's blood line. HDF results in good removal of both large and small molecular weight solutes.

In alternative embodiments, the present disclosure provides methods including circulating a dialysis fluid in a fluid circuit of a dialysis technology or apparatus incorporating one or more of the dialysis devices 2, 100 and 200 in the form of a sorbentless or reduced sorbent cartridge. The dialysis apparatus used in these methods can be a wearable dialysis device.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis fluid treatment device comprising:
   a first cell comprising a first electrodialysis unit configured to generate a cation flow stream, a first neutral flow stream, and a first anion flow stream;
   a second cell comprising at least one of a urease compartment and a sorbent compartment and in fluid communication with the first anion flow stream and the first neutral flow stream of the first cell, the second cell configured to generate a second neutral flow stream and a second anion flow stream; and
   a third cell comprising a second electrodialysis unit and in fluid communication with the second neutral flow stream and the second anion flow stream of the second cell.

2. The dialysis fluid treatment device of claim 1, wherein the third cell further comprises an ammonia sorbent.

3. The dialysis fluid treatment device of claim 1, wherein each of the first, second and third cells comprises at least two corresponding fluid pathways.

4. The dialysis fluid treatment device of claim 1, wherein the first cell and the third cell are fixedly contained within a cartridge for a wearable kidney.

5. The dialysis fluid treatment device of claim 1, wherein the second cell is removably attached to a cartridge for a wearable artificial kidney.

6. The dialysis fluid treatment device of claim 1, wherein the first cell comprises at least one of a cation exchange membrane and an anion exchange membrane.

7. The dialysis fluid treatment device of claim 1, wherein the third cell comprises at least one of a cation exchange membrane and an anion exchange membrane.

8. The dialysis fluid treatment device of claim 1 further comprising an activated carbon unit in fluid communication with the first cell.

9. The dialysis fluid treatment device of claim 1, wherein the second cell is removably attached from and in fluid communication with the first cell and the third cell.

10. The dialysis fluid treatment device of claim 1 further comprising a supplementary ammonia sorbent unit in fluid communication with at least one of the second neutral flow stream and the second anion flow stream.

11. A dialysis fluid treatment device comprising:
    a first cell comprising an electrodialysis unit having a cathode and first and second anodes at opposing ends of the first cell, wherein the cathode and the first anode are provided with a first electrodialysis compartment, and wherein the cathode and the second anode are provided with a second electrodialysis compartment; and
    a second cell comprising a urease compartment and a sorbent compartment and in fluid communication with the first cell,
    wherein the first electrodialysis compartment is in fluid communication with the sorbent compartment by a first flow path and with the urease compartment by a second flow path, and wherein the second electrodialysis compartment is in fluid communication with the urease compartment by a third flow path.

12. The dialysis fluid treatment device of claim 11, wherein the first cell further comprises an ammonia sorbent.

13. The dialysis fluid treatment device of claim 11, wherein the second cell further comprises at least one of a phosphate binder compartment and an anion exchange sorbent component.

14. The dialysis fluid treatment device of claim 11, wherein the first cell is fixedly contained within a cartridge for a wearable artificial kidney.

15. The dialysis fluid treatment device of claim 11, wherein the second cell is removably attached to a cartridge for a wearable artificial kidney.

16. The dialysis fluid treatment device of claim 11, wherein the first cell comprises at least one of a cation exchange membrane and an anion exchange membrane.

17. The dialysis fluid treatment device of claim 10, wherein the sorbent cartridge of the second cell comprises activated carbon.

18. A method for removing urea from a dialysis fluid, the method comprising:
   circulating the dialysis fluid in a fluid circuit that comprises a dialysis apparatus having a cartridge comprising an electrodialysis unit and a urea removal unit;
   removing urea from the dialysis fluid with the cartridge;
   recirculating the dialysis fluid back to a patient; and
   detaching the urea removal unit from the dialysis apparatus and replacing the urea removal unit with a new urea removal unit.

19. The method of claim 18, which includes allowing the urea removal unit to be separable from the electrodialysis unit of the dialysis apparatus.

20. The method of claim 18, which includes configuring the cartridge to be worn by the patient.

* * * * *